(12) United States Patent
Athinarayanan et al.

(10) Patent No.: US 10,066,028 B1
(45) Date of Patent: *Sep. 4, 2018

(54) METHOD OF FABRICATING BIOCOMPATIBLE CELLULOSE NANOFIBRILS

(71) Applicant: KING SAUD UNIVERSITY, Riyadh (SA)

(72) Inventors: Jegan Athinarayanan, Riyadh (SA); Ali A. Alshatwi, Riyadh (SA); Vaiyapuri Subbarayan Periasamy, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/593,145

(22) Filed: May 11, 2017

(51) Int. Cl.
| | |
|---|---|
| *C08L 1/02* | (2006.01) |
| *B82Y 30/00* | (2011.01) |
| *C08B 1/00* | (2006.01) |
| *C08B 1/08* | (2006.01) |
| *A61L 27/38* | (2006.01) |
| *A61L 27/20* | (2006.01) |
| *D01F 2/02* | (2006.01) |
| *C08J 5/18* | (2006.01) |

(52) U.S. Cl.
CPC ............... *C08B 1/08* (2013.01); *A61L 27/20* (2013.01); *A61L 27/3834* (2013.01); *C08J 5/18* (2013.01); *D01F 2/02* (2013.01); *C08J 2301/02* (2013.01); *D10B 2509/00* (2013.01)

(58) Field of Classification Search
CPC ............. C08L 1/02; B82Y 30/00; C08B 1/00
USPC .................................. 536/124, 128
See application file for complete search history.

(56) References Cited

U.S. PATENT DOCUMENTS

| | | | |
|---|---|---|---|
| 6,228,213 B1 * | 5/2001 | Hanna | ...................... C08B 15/02 127/37 |
| 9,074,077 B2 * | 7/2015 | Harada | ................... B82Y 30/00 |
| 2004/0126561 A1 | 7/2004 | Chakrabarti et al. | |
| 2006/0127662 A1 | 6/2006 | Chakrabarti et al. | |

FOREIGN PATENT DOCUMENTS

WO    WO 2016/100856    6/2016

OTHER PUBLICATIONS

Reddy et al ("Exploration on the characteristics of cellulose microfibers form Palmyra palm fruits", International Journal of Polymer Analysis and Characterization vol. 21, Issue 4, 2016, pp. 286-295).*
Xu et al., "Isolation and Properties of Cellulose Nanofibrils from Coconut Palm Petioles by Different Mechanical Process", PLOS One, (2015) 10(4), 11 pages.

* cited by examiner

*Primary Examiner* — Shaojia Anna Jiang
*Assistant Examiner* — Everett White
(74) *Attorney, Agent, or Firm* — Richard C. Litman

(57) ABSTRACT

The method of fabricating biocompatible cellulose nanofibrils produces cellulose nanofibrils from used agro-waste *Borassus flabellifer* leaf stalks. The method uses a three-step process, including alkali treatment, bleaching, and acid hydrolysis to produce cellulose nanofibrils, which may be converted to pellets for storage. The pellets may be converted to a transparent film for cell attachment by dispersion in water and heating in a hot air oven. Testing shows that cellulose nanofibrils made by the method easily attract human mesenchymal stem cells and will be applicable for skin tissue engineering applications.

1 Claim, 6 Drawing Sheets

METHOD OF FABRICATING BIOCOMPATIBLE CELLULOSE NANOFIBRILS

BACKGROUND OF THE INVENTION

1. Field of the Invention

The present invention relates to cellulose nanofibrils made from plants, and particularly to a method of fabricating biocompatible cellulose nanofibrils from *Borassus flabellifer* biomass for tissue engineering applications.

2. Description of the Related Art

Globally, plant biomass production has increased exponentially due to its wide range of application. Plant biomass is a sustainable and renewable bio resource for various applications including, for example, biofuel production, bioenergy generation, and production of chemicals. Recently, the use of plant biomass for biomaterial fabrication has become an area of increased research focus. A variety of materials have been derived from plant biomass through different chemical and biological processes, including lignin-based and cellulose-based nanostructures, polymeric foams, thermoplastics, carbon fibers, ultraviolet protection agents, thermally stimulated shape memory elastomers, and scaffolds, among others.

Plant biomass is typically composed of approximately 15-25% lignin, approximately 30-50% cellulose, and approximately 20-40% hemicellulose. In particular, cellulose is a biopolymer mainly occurring in plant biomass and is present in both amorphous and crystalline forms. For example, cellulose, which has a linear polysaccharide of D-glucose subunits linked with β-1,4-glycosidic bonds, is a sustainable, renewable, and abundant organic material that can be used in the above processes.

Cellulose-based nanostructures are attractive in many scientific fields due to their sustainability, renewability, biocompatibility, biodegradability, availability, and environmental friendliness. Additionally, cellulose-based nanostructures have been used in various applications, including, for example, food packaging, bioelectronic devices, biosensors, energy storage devices, fuel cells, flexible bio-batteries, actuators, drug delivery, protein immobilization, and extracellular matrices. Cellulose nanostructures are known by many different names, such as cellulose whiskers, cellulose nanofibers, microcrystalline cellulose, microfibrillated cellulose, nanofibrillated cellulose, cellulose nanocrystals, tunicate cellulose nanocrystals, algae cellulose particles, and bacterial cellulose particles. Biocompatible and highly pure cellulose nanostructures have been derived from a variety of plant resources, including pineapple leaf, bananas, bamboo, wood, garlic straw, *Arundo donax*, sugarcane bagasse, coconut fiber, oil palm trunk, tomato peels, saw dust wastes, cotton linter, *Agave tequilana*, barley, *Phormium tenax*, hemp, rice husk, wheat straw, soy hull, alfa fibers, corncob, among others.

In particular, *Borassus flabellifer*, a member of the Arecaceae family commonly known as palmyra palm, is an important and versatile plant resource found on the Indian subcontinent in Southeast Asia. *Borassus flabellifer* is considered as a miracle tree because every part of the tree has found wide application. Historically, the *Borassus flabellifer* leaf was utilized for roofing, handicrafts and writing manuscripts, and the leaf stalk-based natural fibers have good mechanical strength and high cellulose content. However, no research has been reported on cellulose nanofibril fabrication from *Borassus flabellifer*.

Stem cells are a versatile tool in tissue engineering and regenerative medicine because of their ability to differentiate into neurons, osteocytes, myocytes, adipocytes, hepatocytes, chondrocytes, and astrocytes. Because of their self-renewal and multipotency, stem cells have been used in therapeutic applications for myocardial infarctions, Buerger's disease, Parkinson's disease, nerve injuries, ischemic strokes, osteogenesis imperfecta, osteoarthritis in ankle joints, articular cartilage defects, neurological disorders, bone regeneration, and cartilage repair. However, stem cells are limited in use in therapeutic applications because of the low differentiation efficiency of stem cells in some cell culture media. Thus, there is great interest in developing new sources of cell culture media for human stem cell research and therapeutic applications.

Thus, a method of fabricating biocompatible cellulose nanofibrils solving the aforementioned problems is desired.

SUMMARY OF THE INVENTION

The method of fabricating biocompatible cellulose nanofibrils produces cellulose nanofibrils from used agro-waste *Borassus flabellifer* leaf stalks. The method uses a three-step process, including alkali treatment, bleaching, and acid hydrolysis to produce cellulose nanofibrils, which may be converted to pellets for storage. The pellets may be converted to a transparent film for cell attachment by dispersion in water and heating in a hot air oven. Testing shows that cellulose nanofibrils made by the method easily attract human mesenchymal stem cells and will be applicable for skin tissue engineering applications.

In the method, leaf stalk residues of *Borassus flabellifer* are used as the raw material for the fabrication of cellulose nanofibrils. The method may include drying and pulverizing the *Borassus flabellifer* leaf stalk to obtain a pulverized *Borassus flabellifer* leaf stalk. The pulverized *Borassus flabellifer* leaf stalk is then treated with an alkali solution to obtain alkali-treated *Borassus flabellifer*. The alkali-treated *Borassus flabellifer* is then bleached to obtain bleached *Borassus flabellifer*. Finally, the bleached *Borassus flabellifer* is hydrolyzed in an acid to form the biocompatible cellulose nanofibril.

The nanofibril biocompatibility results suggest that the fabricated cellulose nanofibrils do not alter cell viability, cellular and nuclear morphology, or gene expression of human mesenchymal stem cells (hMSCs). In particular, the cell-based assay results suggest that nanofibril films enhance the adhesion and proliferation of hMSCs. Therefore, *Borassus flabellifer* biomass-derived nanofibrillated cellulose can serve as suitable matrices for stem cell differentiation and tissue engineering applications.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
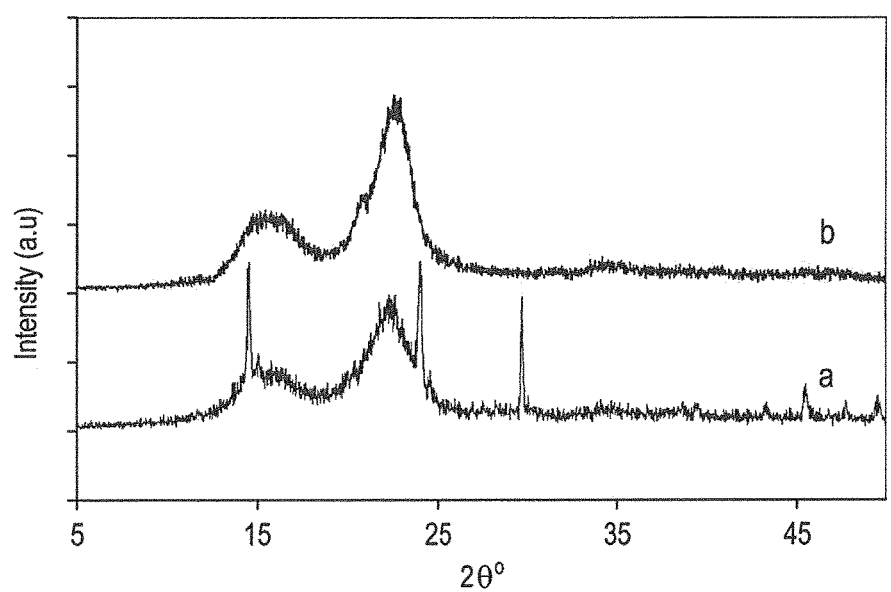
FIG. 1 is a comparison of X-ray diffraction (XRD) spectra of (a) cellulose and (b) cellulose nanofibrils from *Borassus flabellifer* leaf stalk.

The method of fabricating biocompatible cellulose nanofibrils produces cellulose nanofibrils from used agro-waste *Borassus flabellifer* leaf stalks. The method uses a three-step process, including alkali treatment, bleaching, and acid hydrolysis to produce cellulose nanofibrils, which may be converted to pellets for storage. The pellets may be converted to a transparent film for cell attachment by dispersion in water and heating in a hot air oven. Testing shows that cellulose nanofibrils made by the method easily attract human mesenchymal stem cells and will be applicable for skin tissue engineering applications.

For purposes of this disclosure, *Borassus flabellifer* "agro-waste", "biomass", or "leaf stalk" generally refer to various stages of leaf stalk or leaf stalk residues of *Borassus flabellifer*, and can be used interchangeably, except as otherwise provided.

The physicochemical and biocompatibility properties of the cellulose nanofibrils fabricated by the present method were assessed according to various methods. For example, XRD results suggest that the presently fabricated cellulose nanofibrils have a highly crystalline structure. TEM images also show fibrillated cellulose nanostructures that are about 5-20 nm in diameter and about 1-5 µm in length. The nanofibril biocompatibility results suggest that nanofibrils do not alter cell viability, cellular and nuclear morphology, or gene expression of hMSCs. Furthermore, cell-based assay results suggest that nanofibril films enhance the adhesion and proliferation of hMSCs and that *Borassus flabellifer* biomass-derived nanofibrillated cellulose can serve as a suitable matrix for stem cell differentiation in tissue engineering applications.

In particular, raw *Borassus flabellifer* leaf stalk contains a high proportion of hemicellulose and lignin. Pretreatment (alkali treatment and bleaching) of *Borassus flabellifer* leaf stalk efficiently eliminates the hemicellulose and lignin content and increases the cellulose content. Alkali treatment removes hemicellulose and lignin from various biomasses due to the cleavage of ether bonds between lignin and hemicellulose. After alkali and sodium hypochlorite treatment, the color of the *Borassus flabellifer* leaf stalk changes to white, indicating extraction of a large amount of cellulose. The cellulose is then treated with sulfuric acid to form cellulose nanofibrils.

The three-step process generally includes alkali treatment, bleaching, and acid hydrolysis. The alkali treatment and bleaching process eliminates non-cellulosic components from the *Borassus flabellifer* agro-waste. In our experiments, after alkali treatment, the percentage of hemicellulose and lignin decreased from 23.34% and 32.78% to 8.34% and 11.78%, respectively. The cellulose nanofibrils can be fabricated from *Borassus flabellifer* agro waste, leaf stalk, or other parts of the *Borassus flabellifer* plant.

First, the method may include drying the *Borassus flabellifer* leaf stalk to remove a substantial portion of the water content in the leaf stalk. Then, the dried leaf stalk is finely ground to obtain a pulverized *Borassus flabellifer* leaf stalk. The leaf stalk can be ground according to any common method known to one skilled in the art.

The pulverized *Borassus flabellifer* leaf stalk is then treated with an alkali solution to obtain alkali-treated *Borassus flabellifer*. In our experiments, the alkali solution is a 4% sodium hydroxide solution. The pulverized *Borassus flabellifer* leaf stalk may be immersed in the 4% sodium hydroxide solution at 120° C. for 3 hours. After the *Borassus flabellifer* leaf stalk is treated with the alkali solution, the alkali-treated *Borassus flabellifer* is washed. For example, the alkali-treated *Borassus flabellifer* can be twice washed with distilled water to remove the alkali solution from the leaf stalk.

After washing the alkali-treated *Borassus flabellifer*, the *Borassus flabellifer* is bleached to obtain bleached *Borassus flabellifer*. The *Borassus flabellifer* is bleached using a 1:1 solution comprising acetate buffer and 1.7% sodium hypochlorite. The bleached *Borassus flabellifer* is subsequently washed until the pH of the resulting solution is neutral. The washed *Borassus flabellifer* can then be dried at 50° C.

Finally, the dried *Borassus flabellifer* is hydrolyzed in an acid to substantially form the biocompatible cellulose nanofibril. The *Borassus flabellifer* is preferably hydrolyzed in a solution of 64% sulfuric acid. The 64% sulfuric acid solution can be stirred with the *Borassus flabellifer* at 45° C.

The method may further include diluting hydrolyzed *Borassus flabellifer* ten-fold with distilled water to obtain a *Borassus flabellifer* solution. The *Borassus flabellifer* solution is then centrifuged to obtain a pellet of the biocompatible cellulose nanofibril. The cellulose nanofibril from *Borassus flabellifer* fabricated from the exemplary method is biocompatible with human mesenchymal stem cells.

The method is exemplified in the following examples. In these examples, *Borassus flabellifer* leaf stalk was collected from Tirunelveli, India. Sodium hydroxide, sodium hypochlorite, acetic acid and sulfuric acid were obtained from Sigma Chemicals, USA. Eagle minimum essential medium (EMEM), trypsin-EDTA, 3-(4,5-dimethylthiazol-2-yl)-2,5-diphenyltetrazolium bromide (MTT), dimethyl sulfoxide (DMSO), acridine orange, and ethidium bromide were obtained from Sigma-Aldrich (St. Louis, Mo., USA). Fetal bovine serum (FBS) and penicillin-streptomycin were purchased from Invitrogen (Carlsbad, Calif., USA). Double-distilled water was used for all experiments.

Example 1

Preparation of Cellulose Nanofibrils

A sample of *Borassus flabellifer* leaf stalk agro-waste was collected from Tirunelveli, India, and subsequently dried and pulverized. A total of 10 g of the agro-waste was immersed in a 4% sodium hydroxide solution and kept at 120° C. for 3 h. The alkali-treated agro-waste was washed twice with distilled water to remove the remaining alkali solution and dried at 50° C. for 8 h. The sample was then bleached at 90° C. for 3 h using a 1:1 solution of acetate buffer (27 g NaOH and 75 mL acetic acid in 1 L water) and 1.7% sodium hypochlorite. The bleached agro-waste sample was washed until the pH of the material was neutral and dried at 50° C. for 8 h. It was then mixed with a solution of 64% sulfuric acid (8.75 mL/g) at 45° C. for 30 min under stirring. Following hydrolysis, the solution was diluted ten-fold with distilled water and centrifuged at 5000 rpm for 10 min. The obtained pellet was washed with water and ultrasonicated for 15 min. The sample was then centrifuged and dried for further physico-chemical characterization.

Example 2

Cellulose Nanofibril Film Preparation

The cellulose nanofibrils were dispersed in water and poured into a petri dish, which was kept in a hot air oven at 50° C. until the sample was dry. The obtained transparent film was used for cell attachment studies.

Example 3

FTIR Testing

Samples of raw, bleached and cellulose nanofibrils prepared according to Example 1 were characterized by Fourier Transform Infrared (FTIR) spectroscopy. Fourier transform infrared (FTIR) spectra of the samples were measured using a smart performer (attenuated total reflectance (ATR) accessory) with the Nicolette Nexus 470. In the FTIR spectra, three regions were compared: (i) from 3600 to 3000 cm$^{-1}$, corresponding to the —OH stretching of cellulose, which is associated with the hydrogen bonding pattern; (ii) between 1500 and 1200 cm$^{-1}$, related to the $CH_2$ wagging and COH in-plane bending; and (iii) from 1180 to 800 cm$^{-1}$. The results indicate that alkali treatment and bleaching remove the hemicellulose and lignin fractions from *Borassus flabellifer* leaf stalk.

Example 4

X-Ray Diffraction Studies

The crystalline structures of cellulose nanofibrils fabricated as in Example 1 and bleached agro-wastes were analyzed using X-ray diffraction. In particular, the crystalline nature of fabricated samples was investigated using an X-ray diffractometer with Cu Kα=1.5406 A° radiation. FIG. 1 shows the XRD pattern of the (a) bleached *Borassus flabellifer* leaf stalk and (b) cellulose nanofibrils. Bleached leaf stalk shows several peaks at 2Θ=13.72°, 14.9°, 21.72°, 24.04°, 29.68°, 45.3°, 47.2° and 49.3°. The peaks at 14.7° and 21.72° correspond to cellulose, and the other peaks correspond to impurities. In (b) (the cellulose nanofibrils spectrum), two diffraction peaks were observed at 2Θ with a value of 14.90 and 22.5°, corresponding to the (101) and (002) crystallographic planes, respectively. These peaks are due to the cellulose structure, and no other impurities were observed.

Example 5

TEM Imaging

Figure 2A:
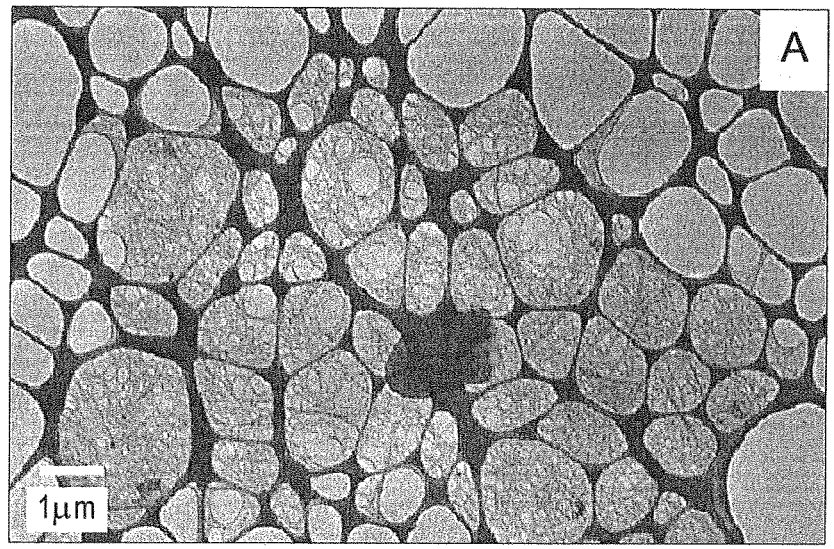
FIG. 2A is a Transmission Electron Microscopy (TEM) micrograph of cellulose nanofibrils from *Borassus flabellifer* leaf stalk at 1 μm.
Figure 2B:
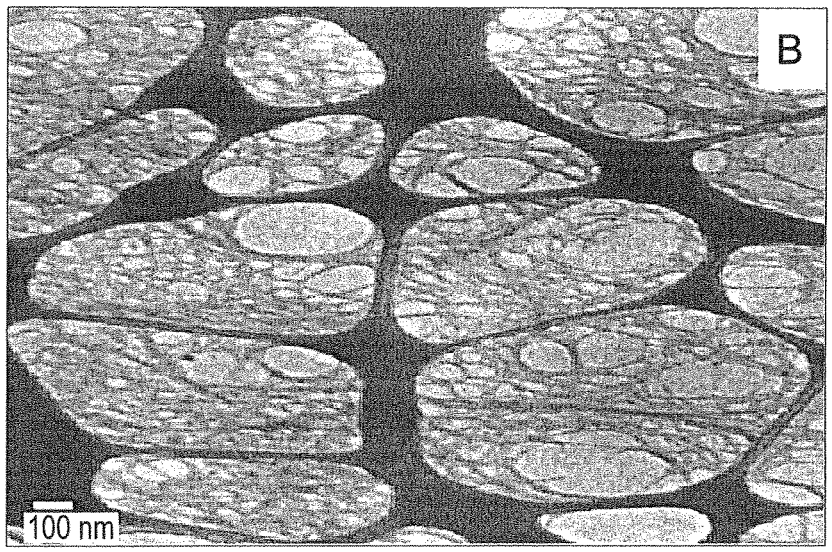
FIG. 2B is a TEM micrograph of cellulose nanofibrils from *Borassus flabellifer* leaf stalk at 100 nm.

The structure and morphology of the fabricated cellulose nanofibrils were analyzed using a transmission electron microscope (JEOL 2010F, USA). The cellulose nanofibrils were sonicated and placed on a carbon-coated copper grid for TEM analyses. FIGS. 2A and 2B show TEM images of the cellulose nanofibrils obtained from *Borassus flabellifer* leaf stalk as in Example 1. Specifically, the TEM images show the fibrillated structure of isolated cellulose at the nanoscale level. The nanofibrils are about 5-20 nm in diameter and 1-5 μm in length and are interconnected through a web-like structure. This type of cellulose nanofibril structure is highly suitable for biomedical applications. These TEM results demonstrate that the present method steps, including alkali treatment, bleaching, and acid hydrolysis, can fabricate suitable cellulose nanofibrils from the *Borassus flabellifer* leaf stalk.

Example 6

Thermogravimetric Analysis

Figure 3:
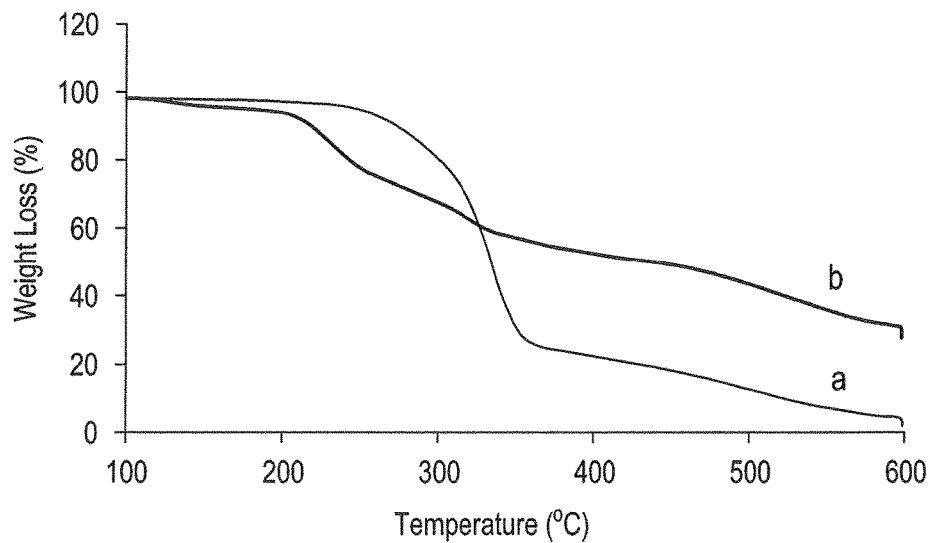
FIG. 3 is a plot of Thermal Gravimetric Analysis (TGA) results of (a) cellulose and (b) cellulose nanofibrils from *Borassus flabellifer* leaf stalk.

The thermal properties of the prepared biocompatible cellulose nanofibrils are critical for their use in biomedical applications. The thermal stability of fabricated cellulose nanofibrils and its precursors were evaluated using TA instrument model Q500-153. The 5.5±1 mg samples were heated at 10° C./min to a final temperature of 600° C. FIG. 3 shows the thermogravimetric analysis (TGA) of (a) cellulose and (b) cellulose nanofibrils derived from the *Borassus flabellifer* leaf stalk as in Example 1. In particular, Curve "a" of FIG. 3 shows the TGA curve of cellulose, which indicates slight weight loss at 200° C. to 250° C. due to loss of moisture. The significant weight loss observed at 300° C. to 400° C. suggests cellulose degradation. In curve "b" of FIG. 3, the cellulose nanofibrils have increased weight loss at 150° C. because of the high number of sulfate groups on cellulose nanofibrils. When the temperature was increased to 220° C., high weight loss was observed due to the degradation of cellulose. In comparison to cellulose, cellulose nanofibrils have low thermal stability due to the presence of sulfate groups. When the number of sulfate groups increases on the surface of cellulose nanofibrils, the degradation rate also increases at lower temperatures.

Example 7

Cell Viability Tested by MTT Assay

Figure 4:
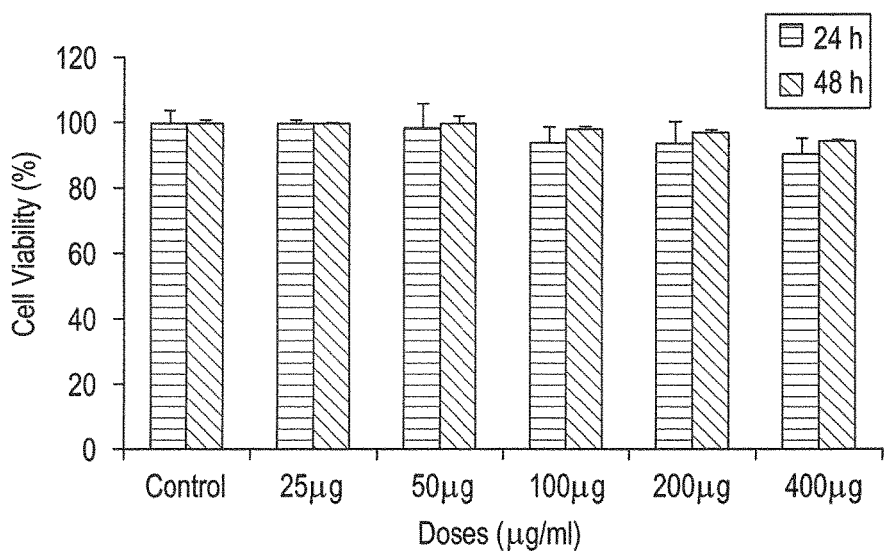
FIG. 4 is a histogram showing the effect of cellulose nanofibrils on hMSC cell viability evaluated by an MTT assay.

Biocompatibility is also an essential characteristic of biomaterials used in biomedical applications. The biocompatibility of the prepared cellulose nanofibrils were assessed using a cell viability assay and cellular and nuclear morphological analyses. The hMSCs were cultured in EMEM and maintained in a $CO_2$ incubator with 5% $CO_2$ at 37° C. The effect of cellulose nanofibrils on cell viability of hMSC was assessed using the MTT assay. The hMSCs were seeded in 96-well plates at a density of $1\times10^4$ cells per well. After 24 h incubation, the cells were treated with various concentrations of cellulose nanofibrils (0-400 µg/mL) and incubated for an additional 24 or 48 h. Afterwards, treated cells were incubated with 20 µL of 3-(4,5-dimethylthiazol-2-yl)-2,5-diphenyltetrazolium bromide solution for 4 h at 37° C. After incubation, the plates were centrifuged, and the suspension medium was discarded. The remaining bluish purple formazan crystals were dissolved in 100 µl of DMSO and read in a microplate reader (Bio-Rad, CA, USA) at 570 nm. Data were collected in triplicate, and the percentage of cell viability was calculated. FIG. 4 shows the effect of cellulose nanofibrils on hMSC cell viability. When the concentration of cellulose nanofibrils was increased from 25 to 400 µg/mL, cell viability decreased from 99 to 90% at 24 h. Moreover, the cell viability declined from 99 to 94% with an increase in nanofibril concentration from 25 to 400 µg/mL at 48 h. In any case, cell viability did not decrease to less than 90% at a high concentration (400 µg/mL) of cellulose nanofibrils. The cellulose nanofibrils reduced the cell viability in a dose/time dependent manner. In fact, the cell viability increased with increasing cellulose nanofibril treatment incubation time, indicating that cell growth is retained after 48 h. These cell viability assay results strongly indicate that cellulose nanofibrils are biocompatible with hMSCs, and thus are potentially suitable for biomedical applications.

Example 8

Cellular and Nuclear Morphology Studies

Cellular and nuclear morphology studies were carried out using bright field and fluorescence microscopy, respectively. For cellular morphology, the hMSCs were seeded in 12-well plates and incubated for 24 h. After 24 h, the cells were exposed to different doses (Dose 1=25 µg/mL, Dose 2=50 µg/mL, Dose 3=100 µg/mL, Dose 4=200 µg/mL and Dose 5=400 µg/mL) of cellulose nanofibrils for 24 and 48 h. The cellular morphology was observed under a bright field microscope. For nuclear morphology, the AO/EB (acridine orange/ethidium bromide) staining assay was used to analyze the nuclear morphology changes in cellulose nanofibril exposed cells. The hMSCs were seeded in 12-well plates and treated with different concentrations of cellulose nanofibrils (Dose 1=25 µg/mL, Dose 2=50 µg/mL, Dose 3=100 µg/mL, Dose 4=200 µg/mL and Dose 5=400 µg/mL) for 24 and 48 h. Control cells were grown in the same way without cellulose nanofibrils. After incubation, cells were washed and treated with the AO/EB dual stain and were observed using a fluorescence microscope (Carl Zeiss, Jena, Germany). The bright field and fluorescence microscopic images showed that the cell morphology and cell growth appeared to be healthier in the cellulose nanofibril-treated cells, and no morphological changes were observed when compared with the control. In the fluorescent images, the corresponding acridine orange/ethidium bromide (AO/EB) stained cell images suggested that cellulose nanofibrils do not cause any significant changes in cell growth, and no dead cells were observed in the fluorescence images. The microscopic analysis results were consistent with cell viability results. The hMSCs that were exposed to increased incubation times with cellulose nanofibrils showed no differences in growth and morphology when compared with the control. The bright field and fluorescence microscopic images clearly demonstrate the excellent biocompatibility of cellulose nanofibrils.

Example 9

Morphological Analysis of hMSCs on Cellulose Nanofibril Film

A morphological analysis of hMSCs on cellulose nanofibril film prepared as in Example 2 at different time intervals (Day 1, Day 3, Day 5 and Day 7) using the AO/EB staining assay was performed. The cellulose nanofibril-based film was fabricated to analyze the hMSCs' attachment and proliferation. The cellulose nanofibril film was fixed in the non-adherent cell culture plates and sterilized under UV light. Subsequently, the cellulose nanofibril film was washed with phosphate buffer solution and re-suspended with cell culture media. The hMSCs were seeded on the surface of cellulose nanofibrils at a density of $1\times10^5$ cells per well. After 24 h incubation, the cell viability and cellular morphology was monitored every day and the cell culture media was changed every 3 days. The resulting images for each respective day confirm that cellulose nanofibrils increase the hMSC adhesion and proliferation. In other words, this clearly demonstrates that cellulose nanofibrils easily attract hMSCs and are applicable for skin tissue engineering applications.

Example 10

Effect of Cellulose Nanofibrils on hMSC Gene Expression

Specifically, the mRNA levels of GPX1, p53, E2F1, NOS1, PCNA, and POR genes were studied to investigate the biocompatibility of cellulose nanofibrils at the molecular level in human mesenchymal stem cells. FIGS. 5A-5F show the effect of the cellulose nanofibrils (Dose 1=50 µg/mL and Dose 2=200 µg/mL) on hMSCs gene expression at 24 and 48 h periods for GPX1, p53, E2F, NOS1, PCNA, and POR.

The cellulose nanofibrils effect on gene expression was studied using reverse transcription-PCR (RT-PCR; Applied Biosystems 7500 Fast, Foster City, Calif.) with the real-time SYBR Green/ROX gene expression assay kit. The hMSCs were seeded in 24 well plates at the density of $5\times10^4$ cells per well. After overnight, the cells were exposed to Dose 1=50 g/mL and Dose 2=200 µg/mL of cellulose nanofibrils for 24 and 48 h. After incubation, cDNA was synthesized from nanofibrillated cellulose-treated and untreated hMSCs using a Fastlane® Cell cDNA Kit. The mRNA levels of glutathione peroxidase (GPX1), tumor suppressor protein (p53), E2F1 (E2F Transcription Factor 1), NOS1 (Nitric Oxide Synthase 1), PCNA (Proliferating cell nuclear antigen), POR (cytochrome p450 oxidoreductase) and the reference gene glyceraldehyde 3-phosphate dehydrogenase (GAPDH) were assayed using gene-specific SYBR Green-based QuantiTect® Primer Assays. According to manufacturer's instructions, a 25 µL reaction volume was used in each well of the PCR plates. Briefly, 12.5 L of master mix, 2 µL of assay primer (10×) and 10 µL of template cDNA (500 pg) were added to each well. After centrifugation, the PCR plate was subjected to 40 cycles under the following conditions: (i) PCR activation at 95° C. for 5 minutes, (ii) denaturation at 95° C. for 5 seconds, and (iii) annealing/extension at 60° C. for 30 seconds. Quantitative RT-PCR data were analyzed using the comparative threshold (Ct)

method, and fold inductions of samples were compared with the control. GAPDH was used as an internal reference gene to normalize the expression of the target genes. The Ct method was used to determine the expression level in untreated and nanofibrillated cellulose-treated hMSCs for 24 and 48 h. The results are expressed as the ratio of the reference gene to the target gene using the following formula: ΔCt=Ct (target genes)−Ct (GAPDH). To determine relative expression levels, the following formula was used: ΔΔCt=ΔCt (Treated)−ΔCt (untreated control). Thus, expression levels are expressed as n-fold differences relative to the reference gene. The value was used to plot the expression of target genes using the expression of 2-ΔΔCt. The results were obtained from three independent experiments.

Figure 5A:
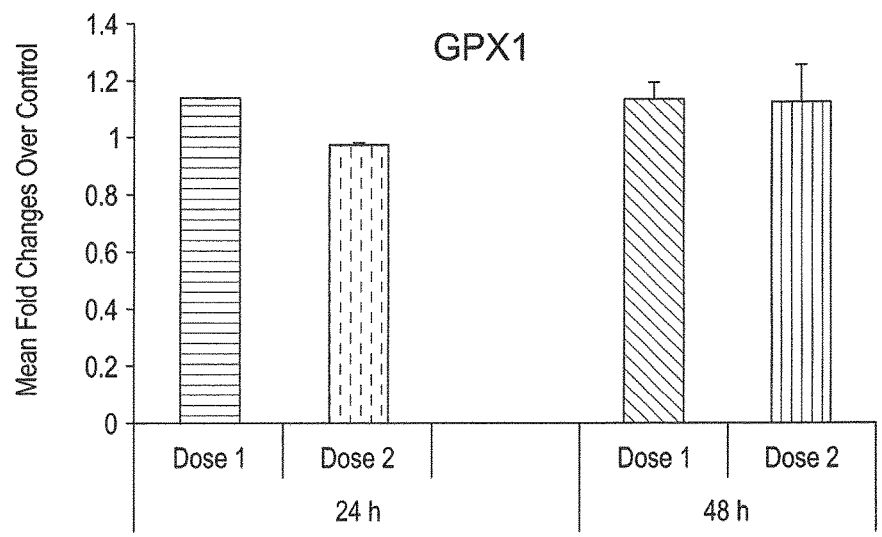
FIG. 5A is a plot showing the effect of dosages of cellulose nanofibrils on GPX1 gene expression of hMSC after 24 hours and after 48 hours as mean fold changes over a control sample.

The GPX1 gene is an antioxidant enzyme that prevents intracellular hydrogen peroxide accumulation. FIG. 5A shows the effect of the cellulose nanofibrils on GPX1. The graph indicates that GPX1 gene expression was both dose and time dependent in cellulose nanofibril treated hMSCs. However, no significant changes were observed in GPX1 gene expression.

Figure 5B:
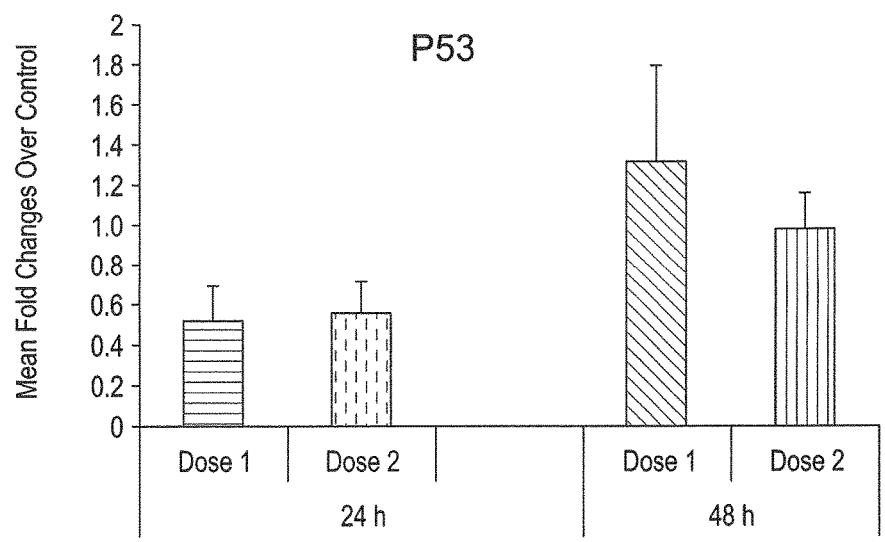
FIG. 5B is a plot showing the effect of dosages of cellulose nanofibrils on P53 gene expression of hMSC after 24 hours and after 48 hours as mean fold changes over a control sample.

The p53 gene is involved in several cellular processes including apoptosis, cell growth arrest, genome stability, and senescence. FIG. 5B shows the effect of the cellulose nanofibrils on p53 gene expression. The p53 gene expression level slightly increased in cellulose nanofibrils treated cells, when compared with control. The results indicate that cellulose nanofibrils do not induce apoptosis and cell proliferation inhibition in hMSCs. These results are consistent with cellular and nuclear morphological changes in nanofibril treated hMSCs.

Figure 5C:
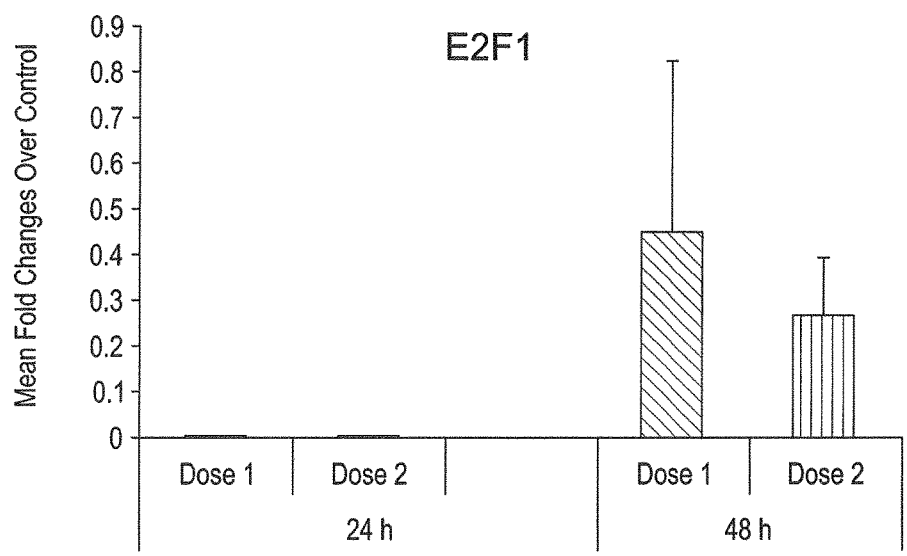
FIG. 5C is a plot showing the effect of dosages of cellulose nanofibrils on E2F1 gene expression of hMSC after 24 hours and after 48 hours as mean fold changes over a control sample.

The E2F1 gene plays an important role in cell cycle progression. FIG. 5C shows the effect of the cellulose nanofibrils on E2F1 gene expression. After 24 h treatment, no changes were observed in the expression level of E2F1 gene in hMSCs. This indicates that cellulose nanofibrils do not cause any changes in cell cycle and proliferation. Moreover, p53 and E2F1 gene expression suggested that cellulose nanofibrils have excellent biocompatibility with hMSCs.

Figure 5D:
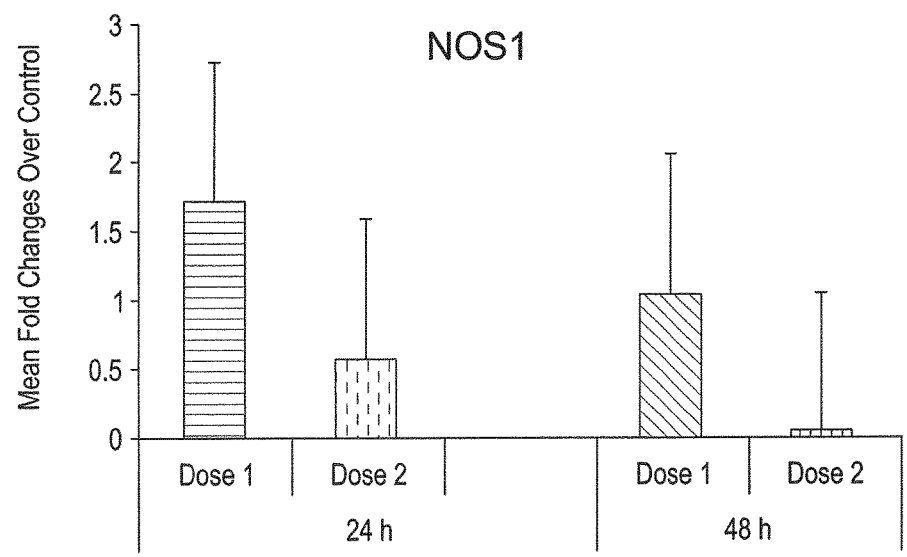
FIG. 5D is a plot showing the effect of dosages of cellulose nanofibrils on NOS1 gene expression of hMSC after 24 hours and after 48 hours as mean fold changes over a control sample.

The enzyme NOS1 is a nitric oxide synthase that mainly regulate cell death and neurodegeneration. FIG. 5D shows the effect of the cellulose nanofibrils on NOS1 gene expression. The cellulose nanofibrils slightly increased the expression level of NOS1 at low concentration. Further, the expression level of NOS1 decreased with increasing dose and time of exposure.

Figure 5E:
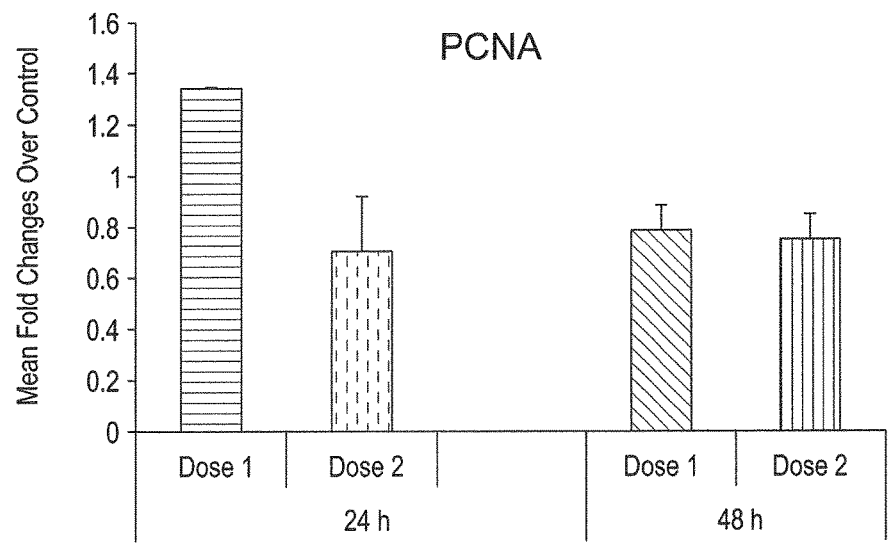
FIG. 5E is a plot showing the effect of dosages of cellulose nanofibrils on PCNA gene expression of hMSC after 24 hours and after 48 hours as mean fold changes over a control sample.
Figure 5F:
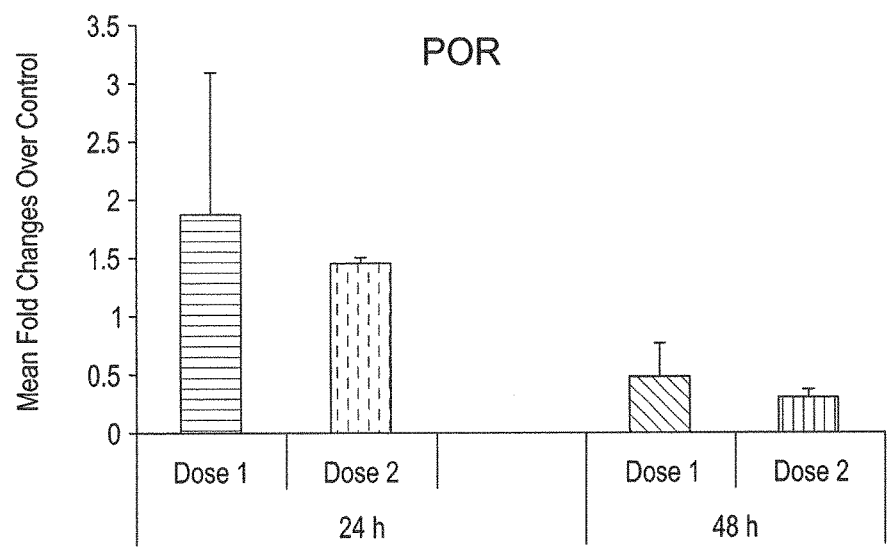
FIG. 5F is a plot showing the effect of dosages of cellulose nanofibrils on POR gene expression of hMSC after 24 hours and after 48 hours as mean fold changes over a control sample.

Lastly, as shown in FIG. 5E and FIG. 5F, PCNA and POR gene expression decreased when the dose and time in cellulose nanofibril treated hMSCs increased. This indicates that cellulose nanofibrils have excellent biocompatibility with hMSCs.

It is to be understood that the present invention is not limited to the embodiments described above, but encompasses any and all embodiments within the scope of the following claims.

We claim:

1. A method of fabricating biocompatible cellulose nanofibrils, comprising the steps of:

drying *Borassus flabellifer* leaf stalk;

pulverizing the dried *Borassus flabellifer* leaf stalk to obtain a pulverized *Borassus flabellifer* leaf stalk;

immersing the pulverized *Borassus flabellifer* leaf stalk in a 4% sodium hydroxide solution at 120° for 3 hours to obtain alkali-treated *Borassus flabellifer*;

washing the alkali-treated *Borassus flabellifer* leaf stalk to remove alkali;

drying the alkali-treated *Borassus flabellifer* leaf stalk at 50° C. for 8 hours;

bleaching the dried, alkali-treated *Borassus flabellifer* leaf stalk using a 1:1 solution of acetate buffer and 1.7% sodium hypochlorite at 90° C. for 3 hours to obtain cellulose-enriched *Borassus flabellifer* residue;

washing the cellulose-enriched *Borassus flabellifer* residue until reaching a neutral pH;

drying the washed cellulose-enriched *Borassus flabellifer* residue at 50° C. for 8 hours;

mixing and stirring the dried cellulose-enriched *Borassus flabellifer* residue with a solution of 64% sulfuric acid at 45° C. for 30 minutes to obtain cellulose nanofibrils from the cellulose in the *Borassus flabellifer* residue;

diluting the obtained cellulose nanofibrils ten-fold with distilled water;

centrifuging the diluted cellulose nanofibrils at 5000 rpm for 10 minutes to obtain a pellet; and ultrasonicating the pellet for 15 minutes.

* * * * *